US005932242A

United States Patent [19]
Franklin et al.

[11] Patent Number: 5,932,242
[45] Date of Patent: Aug. 3, 1999

[54] ETHER LIPID-CONTAINING PHARMACEUTICAL COMPOSITIONS AND THERAPEUTIC USES THEREOF

[75] Inventors: J. Craig Franklin, East Windsor; Eric Mayhew, Monmouth Junction; Walter Perkins, Skillman, all of N.J.; Andrew Janoff, Yardley, Pa.

[73] Assignee: The Liposome Company, Inc., Princeton, N.J.

[21] Appl. No.: 08/720,997

[22] Filed: Oct. 15, 1996

[51] Int. Cl.$^6$ .................................................. A61K 9/127
[52] U.S. Cl. ............................................................. 424/450
[58] Field of Search ........................... 424/450; 436/829; 428/402.2

[56] References Cited

U.S. PATENT DOCUMENTS

| | | | |
|---|---|---|---|
| 3,752,886 | 8/1973 | Munder et al. | 424/199 |
| 4,426,525 | 1/1984 | Hozumi et al. | 546/22 |
| 4,734,225 | 3/1988 | Eibl | 260/386 |
| 4,804,789 | 2/1989 | Eibl | 568/853 |
| 4,965,391 | 10/1990 | Counsell et al. | 558/169 |
| 4,983,397 | 1/1991 | Schroit et al. | 424/450 |
| 5,077,057 | 12/1991 | Szoka, Jr. | 436/829 |
| 5,169,637 | 12/1992 | Lenk et al. | 514/192 |

FOREIGN PATENT DOCUMENTS 4132345  4/1993  Germany.

OTHER PUBLICATIONS

Bazill, et al., "Role of Endocytosis in the Action of Ether Lipids on WEHI–3B, HL60, and FDCP–Mix A4 Cells", Cancer Research, 50, 7505–7512, Dec. 1, 1990.
Berdel, "Ether Lipids and Derivatives as Investigational Anticancer Drugs", Onkologie 1990:13:245–250.
Bhatia, et al., "Stereospecific Synthesis of Antitumor Active Thioether PAF Analogs", Lipids, 26(12), 1424–1430, 1991.
Chen, et al., "Microdetermination of Phosphorus", Anal. Chem.,28 (11), 1756–1758; 1956.
Deamer, et al., "Liposome Preparation: Methods and Mechanisms", in *Liposomes,* Marcel Dekker, ed. M. Ostro, 1983, 27–51.
Dietzfelbinger, et al., "Removal of Breast Cancer Cells from Bone Marrow by in Vitro Purging with Ether Lipids and Cryoperservation", Cancer Research 53, 3747–3751, Aug. 15, 1993.
Gruner, "Nonlamellar Lipis Phases", in *The Structure of Biological Membranes,* 1992, CRC Press, ed. P. Yeagle, Buffalo, NY, pp. 222–223.
Kumar, et al., "Phosphlipid Deitribution and Headgroup Motion in Phosphatidylcholine Liposomes of Different Size", Biophys. J., 53, 1988, 121a.
Layton, et al., "The Interaction of Liposomes with Cells: The Relation of Cell Specific Toxicity to Lipid Composition", Eur J Cancer, 16, 1529–1538, 1980.
Madden, et al., "Stabilization of bilayer Structure for Unsaturated Phosphatidylethanolamines by Detergents", BBA, 684 (1982), 149–153.
Nairn, et al., "Solutions, Emulsions, Suspensions and Extractives", in *Pharmaceutical Sciences,* 1985, Mack Publishing Co., Easton, PA.
Papahadjopoulos, et al. "Phospholipid Model Membranes, I. Structural Characteristics of Hydrated Liquid Crystals", BBA 135 (1967) 624–638.
Powis, et al., "Selective Inhibition of Phosphatidyloinositol Phospholipase C by Cytotoxic Ether Lipid Analogues", Cancer Research 52, 2835–2840, May 15, 1992.
Reed, et al., "Antineoplastic Ether–Linked Phospholipid Inudces Differentiation of Acute Myelogenous Leukemic KG–1 Cells Into Macrophase–Like Cells", Life Sciences,49, 1221–1227, 1991.
Runge, "Destruction of human Solid tumors by Alkyl Lysophospholipids", JNCI, 64(6), Jun. 1980, 1301–1306.
Tritton, et al., "How to Kill Cancer Cells: Membranes and Cell signaling as Targets in Cancer Chemotherapy", Cancer Cells, Apr. 1990, 95–105.
Stedman's Medical Dictionary, pp. 707–708.
Stedman's Medical Dictionary, pp. 123–124.
Workman, "Antitumour Ether Lipids: Endocytosis as a Determinant of Cellular Sensitivity", Cancer Cells, 3(8), 315–317, Aug. 1991.
Workman, et al., "Platelet–activating factor (PAF) antagonist WEB 2086 does not modulate the cytotoxicity of PAF of antitumor alkyl lysophospholipids ET–18–O–Methyl and SRI 62–834 in HL–60 promyelocytic leukaemia cells", Biochemical Pharmacology, 41(2), 319–322, 1991.
Wu, et al., "Modified In Vivo behavior of Liposomes Containing Synthetic Glycolipids", BBA 674 (1981), 19–29.
Zeisig, et al., "Antineoplastic activity in vitro of free an liposomal alklyphosphocholines", Anti–Cancer Drugs, 4, 57–64, 1993.

*Primary Examiner*—Mary E. Ceperley
*Attorney, Agent, or Firm*—Kenneth B. Rubin; Rosanne Goodman

[57] ABSTRACT

Pharmaceutical compositions are provided herein that contain, in addition to a pharmaceutically acceptable carrier, a lamellar lipid. The lipid is composed of an ether lipid and a lipid having a molecular shape that is complementary to the molecular shape of the glycerolipid. These compositions can be used therapeutically, for example, in the treatment of cancers and inflammatory conditions.

21 Claims, 4 Drawing Sheets

ETHER LIPID-CONTAINING PHARMACEUTICAL COMPOSITIONS AND THERAPEUTIC USES THEREOF

FIELD OF THE INVENTION

This invention is directed to ether lipid-containing pharmaceutical compositions, and to the use of such compositions in the treatment of various disorders, e.g., cancer and inflammatory conditions.

BACKGROUND OF THE INVENTION

Cancer chemotherapy generally aims to slow the growth of, or destroy, cancer cells while avoiding collateral damage to surrounding cells and tissues; the most effective anticancer agents are best able to selectively target cancer cells while leaving normal cells relatively unaffected. Some ether lipids can be effective as anticancer agents in animals (see for example, Dietzfelbinger et al. (1993); Zeisig et al. (1993); Powis et al. (1990); Berdel (1991); Bhatia and Hadju (1991); Reed et al. (1991); Workman (1991); Workman et al. (1991); Bazill and Dexter (1990); Berdel (1990); Counsell et al. (1990); Tritton and Hickman (1990); Muschiol et al. (1990); Layton et al. (1980); Runge et al. (1980); Munder & Westphal (1990); Lohmeyer & Workman (1995); Lohmeyer & Bittman (1994); Great Britain Patent No. 1,583,661, Pat. No. 3,752,886).

It is speculated that the lack of alkyl cleavage enzyme expression in cancer cells is responsible for the failure of these cells to hydrolyze and remove the ether lipids, and hence, for the accumulation of the lipids in these cells. This intracellular ether lipid accumulation leads to the disturbance of cell membrane lipid organization by a detergent-like activity of ether lipids. Membrane structure, and hence, cell stability, can be disrupted by this activity.

Normal cells typically possess the alkyl cleavage enzymes required to hydrolyze ether lipids and hence, to prevent their intracellular accumulation. However, normal cells which do not possess the requisite levels of the enzymes, e.g., red blood cells ("RBCs") are subject to the same disruptive effects of ether lipid action as are cancer cells. Hemolysis, which results from exposure of RBCs to ether lipids having detergent-like activity can be a major drawback to therapeutic use of the ether lipids (see, for example, Houlihan et al., 1995).

A number of different approaches are potentially available for decreasing or eliminating such drug-induced toxicity. One approach is to incorporate the drugs into lipid-based carriers, e.g., liposomes. Such carriers can buffer drug toxicity, for example, by sequestering the drug in the carrier such that the drug is unavailable for inducing toxicity. Lipid carriers can also buffer drug-induced toxicity by interacting with the drug such that the drug is then itself unable to interact with the cellular targets through which it exerts its cytotoxic effects. The carriers also maintain the ability of the drugs to be therapeutically effective when released therefrom, e.g., when the carriers are broken down in the vicinity of tumors.

However, the organization and packing arrangements of lipids in lipid-based carriers, e.g., liposomal bilayers, is similar to lipid organization and arrangement in cell membranes. Accordingly, a drug, such as an ether lipid, believed to exert its toxic effects, at least in part, by disrupting cell membrane lipid organization, have the same type of adverse effect on the lipid based carrier. In such cases, for the lipid-based structure to be effective as a carrier it must be formulated such that the toxicity-inducing drug cannot disrupt the carriers structure, but nevertheless is maintained in a form so that, when released from the carrier, the drug is then therapeutically effective.

This invention provides a formulation comprising a lamellar lipid which comprises an ether lipid and a lipid of complementarily molecular shape to the ether lipid. The shape complementarity brought about by the combination of these lipids in a lamella inhibits ether lipids possessing detergent-like activity from exercising it on the lamellae of the carrier. Nevertheless, when the lamellae reach the intended sites of therapeutic action and are then broken down, the ether lipids are released in a therapeutically effective form.

PCT/US95/12721 describes liposomes containing cholesterol, a phosphatidylcholine and a phosphatidylethanolamine-dicarboxylic acid derivative, in addition to a glycerol-based ether lipid having a methoxy group attached to the second position of the glycerol backbone. German Patent Application No. 4,132,345 describes liposomes containing cholesterol and a positively charged lipid in addition to a methoxy group-containing ether lipid. Japanese Patent Application No. 61-022,020 describes liposomes containing cholesterol and a phospholipid in addition to an acetyl, or propionyl, group-containing glycerol-based ether lipid. Mende et al. describes the membrane potential altering effects of liposomes containing an ether lipid/cholesterol combination of an equimolar ratio. However, none of these documents describes pharmaceutical compositions containing glycerol-based ether lipids having a methoxy group at the second position, or the use of such compositions in the treatment of various cancers and inflammatory conditions, amongst other disorders.

SUMMARY OF THE INVENTION

Chemotherapeutic activity of ether lipids is believed to arise, at least in part, from their ability to accumulate in cancer cells, due to the lack in the cells of the alkyl cleavage enzymes necessary for hydrolysis, and hence, removal of these lipids. Exertion of detergent-like activity by ether lipids collected in cancer cell membranes can disturb the structure of the membranes, and hence, disrupt the cells. Most, but not all, normal cells possess the enzymes necessary for ether lipid hydrolysis and removal; however, red blood cells ("RBCs") do not possess these enzymes, and hence, are also susceptible to disruption due to intracellular ether lipid accumulation. Such hemolysis is a major dose-limiting toxicity of ether lipid therapeutic use. However, the red blood cell toxicity can be reduced by sequestering the ether lipid in a lipid based carrier such that the ether lipid and carriers are in a stable structure.

The ether lipid stably sequestered in the lipid carrier is unavailable for interaction with the membranes of normal cells, and therefore cannot disrupt the membranes' lipid structure. Nevertheless, when the ether lipid is released from the carrier, generally upon carrier breakdown in the body, it is then available for therapeutic action against cancer cells. Since tumors generally have a higher concentration of blood vessels than does the surrounding normal tissue, and as tumor vasculature tends to be more leaky to structures such as lipid-based carriers, the carriers will preferentially accumulate in tumors; hence, when broken down ether lipids will preferentially be released in the tumors.

This invention provides a composition containing, in addition to a pharmaceutically acceptable carrier, a lamellar lipid consisting essentially of an ether linkage-containing glycerolipid, i.e., an "ether lipid," and a "complementarily shaped lipid," i.e., a lipid having a shape that is complementary to the molecular of the ether lipid. The glycerolipid has the formula:

wherein $R^1$ is preferably a group having the formula —$(CH_2)_{n1}CH_3$, and more preferably is —$(CH_2)_{17}CH_3$. Z is preferably oxygen. Most preferably, the glycerolipid is:

i.e., "ET-18-OCH$_3$."

The complementarily shaped lipid is preferably a neutral sterol, an anionic sterol derivative, cardiolipin, diarachidonoyl phosphatidylethanolamine ("DAPE") or a similar lipid. More preferably, the complementarily shaped lipid is cholesterol, cholesterol sulfate or a combination of cholesterol and cholesterol sulfate.

The pharmaceutical compositions of this invention can be used therapeutically, for example in the treatment of various cancers and inflammatory conditions, by administering to afflicted mammals an amount of a composition which comprises a therapeutically effective amount of the ether lipid.

BRIEF DESCRIPTION OF THE DRAWINGS

FIG. 1

Surface pressure versus mean molecular area per molecule ("MMAM") for monolayer films of individual lipids. Lipids are ET-18-OCH$_3$ (a), cholesterol (b), POPC (c), DOPC (d), and DOPE (e). Films were compressed at 15 cm$^2$/minute. Each curve is the average of three compressions.

FIG. 2

A) Mean molecular area per molecule as a function of ET-18-OCH$_3$ content where monolayers were formed from ET-18-OCH$_3$ mixed with DOPC (●), POPC (filled Δ), DOPE (■), or cholesterol (filled ▽). Data are the average of 3 experiments, ±S.D. The dashed line represents the expected values (A$_0$) for cholesterol/ET-18-OCH$_3$ mixtures based on simple additivity of the individual MMAM values. B) Percent reduction in MMAM as a function of ET-18-OCH$_3$.

FIG. 3

Hemolytic activity of ET-18-OCH$_3$ incorporated in liposomes formed by extrusion through a 100 nm pore size filter. Symbols represent free ET-18-OCH$_3$ (♦), and ET-18-OCH$_3$ incorporated at 40 mole percent into liposomes with the lipids POPC (●), DOPC (filled Δ), DOPE (■), and cholesterol (filled ▽). Each preparation was run in triplicate, and the error bars represent S.D. Liposome size was measured by dynamic light scattering and found to be approximately 40 nm for samples except ET-18-OCH$_3$/cholesterol liposomes, which had a mean diameter of 77 nm.

FIG. 4

Schematic representation of the effect of lipid molecular shape on collective organization. Darkened regions represent hydrophilic lipid headgroups; shaded regions represent the lipids' hydrophobic hydrocarbon domains.

DETAILED DESCRIPTION OF THE INVENTION

Bioactive lipids of this invention have a three-carbon glycerol backbone and hence, are also known as "glycerolipids." The lipids comprise a hydrocarbon chain ("$R^1$"), the terminal methylene carbon of which is linked to the glycerol backbone at position number 1 of the backbone through an oxygen atom. Hence, the hydrocarbon chain is connected to the glycerol backbone by way of an ether linkage, and the glycerolipids of this invention are "ether linkage-containing glycerolipids" or "ether lipids."

A methyl group is linked to the glycerol backbone at position number 2 of the glycerol backbone, through either an oxygen atom or a sulfur atom, and a phosphorylcholine group (OP(O)$_3$CH$_2$CH$_2$N(CH$_3$)$_3$) is attached at position number 3. Accordingly, the glycerolipid of this invention has the following formula:

$R^1$ is a group having the formula $Y^1Y^2$, wherein $Y^1$ is the group $(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}$. The sum of n1+2n2+n3+2n4+n5+2n6+n7+2n8+n9 is an integer of from 9 to 23; n1 is zero or an integer of from 1 to 23, n3 is zero or an integer of from 1 to 20, n5 is zero or an integer of from 1 to 17, n7 is zero or an integer of from zero to 14 and n9 is zero or an integer of from 1 to 11; each of n2, n4, n6 and 8 is independently zero or 1. $Y^1$ is preferably saturated, having the formula $(CH_2)_{n1}CH_3$ as each of n2, n3, n4, n5, n6, n7 and n8 is then equal to 0. $Y^2$ is C(O)$_2$H or CH$_3$, and is preferably CH$_3$. Accordingly, $R_1$ is preferably (CH$_2$)$_{n1}$CH$_3$. Most preferably, $R^1$ is (CH$_2$)$_{17}$CH$_3$. Z is O or S, but is most preferably O.

Accordingly, the glycerolipid of this invention is most preferably:

that is, 1-O-octadecyl-2-O-methyl-sn-3-phosphorylcholine ("EL-18" or "ET-18-OCH$_3$"). Although the lamellae of this invention can comprise additional, nonlipid, constituents, the lipid component primarily comprises a glycerolipid and a "complementarily shaped lipid," that is a lipid having a molecular shape which is complementary to the molecular shape of the glycerolipid.

Figure 4:
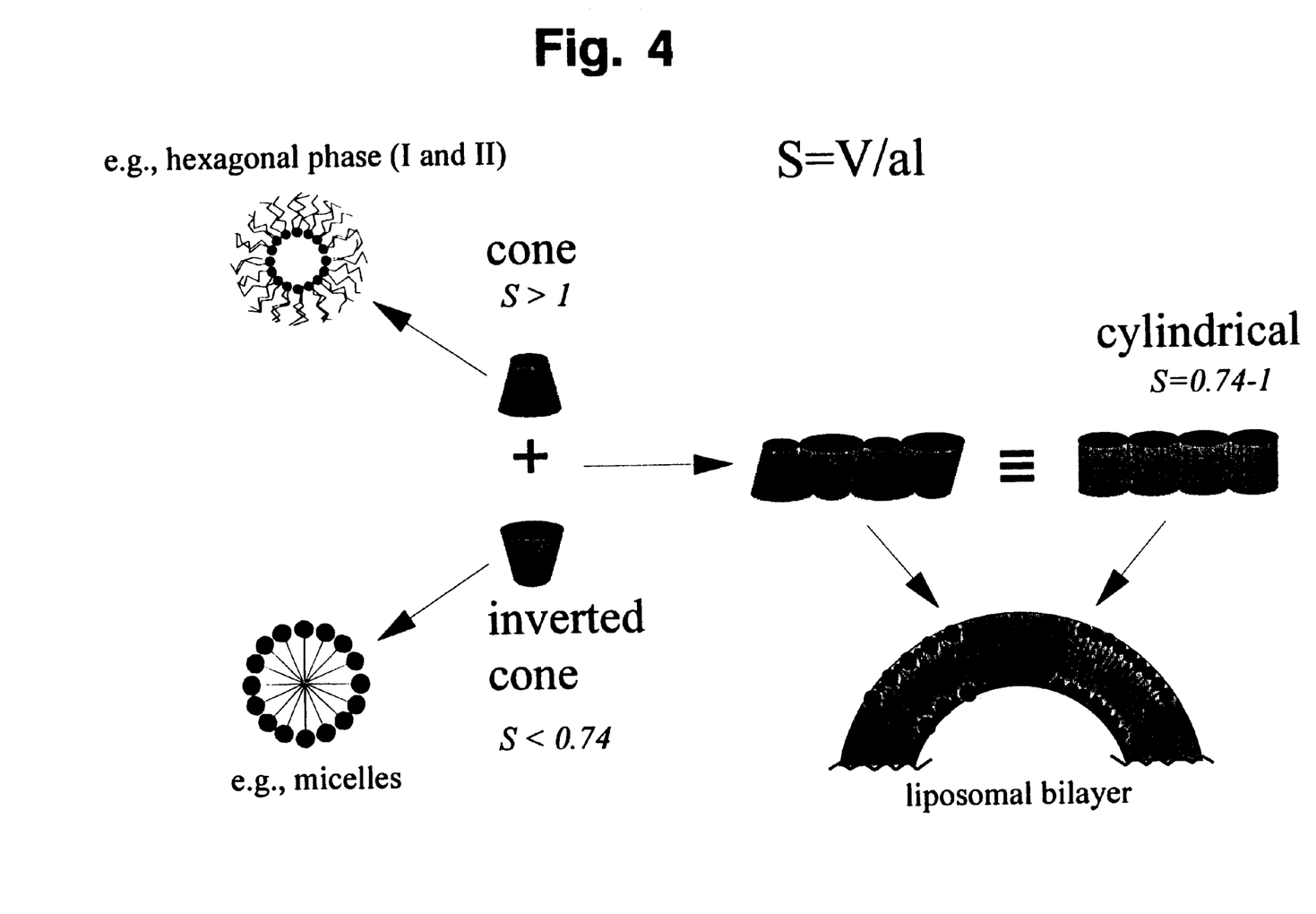

Amphipathic lipids, which comprise a hydrophilic headgroup and a hydrophobic acyl chain domain, have either a cone-shaped, cylindrical or inverted cone-shaped conformation in aqueous environments (see, FIG. 4). The particular shape of hydrated amphipathic lipids depends upon the size of their headgroups relative to the volumes and cross-sectional areas of their hydrophobic domains (see, e.g., Kumar et al., 1991; Rand et al., 1975; Madden & Cullis, 1982; Wu et al., 1991; Wu & Chi, 1991; and, Israelachvili, et al., 1976, the contents of which are incorporated herein by reference). Cone-shaped lipids have headgroup surface areas that are less than cross-sectional areas of their hydrocarbon domains; these lipids form micelles in aqueous environments, wherein the lipid headgroups are arrayed around the micelle exterior while the hydrocarbons are sequestered in the interior. Inverted cone-shaped lipids have headgroup surface areas that are larger than hydrophobic domain cross-sectional areas; these lipids form inverted micelles, wherein the headgroups are arrayed in the structure's interior, and the hydrocarbons are arrayed around the exterior. Cylindrical lipids have headgroups surface areas that are about equal to cross-sectional areas of their hydrophobic domains. These lipids can form bilayers on their own, with their hydrocarbons then being arrayed in a generally planar side-by-side conformation in the bilayer's interior while the lipid headgroups are arrayed towards the surrounding aqueous environment.

Cylindrical lipids are particularly suited to the formation of lamellar structures because of the symmetry they possess along the long axes of their molecules. This symmetry allows the lipids to adopt planar side-by-side conformations consistent with their providing maximal shielding of the hydrophobic hydrocarbons from energetically unfavorable contacts with the surrounding water. Cone-shaped lipids and inverted cone-shaped lipids, with their disparately sized headgroups and hydrocarbon domains, generally do not form lamellae on their own because of their asymmetry of molecular shape. Attempts by cone-shaped lipids and inverted cone-shaped lipids to form planar side-by-side packing arrangements in lamellae would, because of their asymmetric molecular shapes, leave significant portions of the lipids' hydrocarbon domains exposed to the aqueous environment. Micelles, for cone-shaped lipids, and inverted micelles, for inverted cone-shaped lipids, expose less of the hydrocarbon regions of these lipids, and hence, are more energetically favorable structures for these types of lipids.

However, cone-shaped lipids together with inverted cone-shaped lipids can form lamellae. Combination of a cone-shaped lipid with an inverted cone-shaped lipid affords approximate symmetry along the long axes of the combined lipid molecules, and thereby provides maximal shielding for the lipids' hydrocarbon domains in a bilayer structure. Accordingly, a "complementarily shaped lipid" is a lipid having an asymmetric molecular shape which can, together with a second asymmetrically shaped lipid molecule, form a lipid molecular pair having approximate symmetry along the combined molecules' long molecular axes; in the case of inverted cone-shaped molecules, the second asymmetrically shaped lipid is a cone-shaped lipid. Since the glycerolipids of this invention have an inverted cone-shape, the complementarily shaped molecules have a cone-shape.

Moreover, the relative headgroup/hydrocarbon domain size of a lipid can be expressed by the value of the lipid's "packing parameter" ("S"). Packing parameters are determined in accordance with the equation $S=V/(a)(l)$, wherein "V" is the volume of the lipid's hydrocarbon domain, "a" is the lipid's headgroup surface area and "l" is the length of the hydrocarbon chain(s). Cylindrical lipids, with their about symmetrical shape, have a packing parameter of about 0.74–1. Inverted cone-shaped lipids, whose polar regions occupy a relatively larger space than do their hydrophobic domains, have packing parameters of less than about 0.74. Cone-shaped lipids, with their smaller polar regions and relatively larger hydrophobic domains have packing parameters of greater than about 1. Accordingly, as "complementarily shaped lipids" herein are cone-shaped, they also have a packing parameter greater than about 1.

A measure of the amount of space occupied by a lipid molecule is the mean area ("MMAM") that a molecule of the lipid occupies in a monolayer formed of that lipid. MMAM values for various lipids can readily be determined by ordinarily skilled artisans given the teachings of this invention, for example, as set forth in Example 1 below. MMAM values can be determined by first forming a lipid monolayer on the surface of an aqueous medium contained within a suitable trough, by the drop-wise addition of a lipid solution to the surface of the aqueous medium. Lipid solution is continuously added to the medium's surface, until the surface pressure commences to increase; the confines of the trough are then decreased, such that surface area is also decreased. Surface pressures for the different surface areas are recorded, and area-vs.-pressure curves compiled. MMAM values are obtained from these curves by extrapolating the steepest portion of the curve to a lipid's surface area at zero pressure.

The mean area occupied by a lipid molecule in a monolayer formed by a combination of cone-shaped and inverted cone-shaped lipids could be calculated according to the equation $A_0=X^1 \cdot A^1+X^2 \cdot A^2$ (see Ali et al., the contents of which are incorporated herein by reference), wherein "$A_0$" is the MMAM expected of the lipids in the two component system, $X^1$ and $X^2$ are the relative mole percentages of the lipids in the combination, and $A^1$ and $A^2$ are the measured MMAM values of the individual lipids. Accordingly, the combination of lipids in a two-component monolayer would be expected to result in a mean molecular area per lipid molecule ("$MMAM_{expected}$") reflective of the relative proportions in which each of the constituent lipids is present in the combination. That is, calculated in accordance with the above equation, the MMAM value expected of the lipids would be additive.

However, additivity of MMAM values is not the case when a glycerolipid is combined with a complementarily shaped lipid in the lipid lamellae of this invention. Rather, when the mean molecular area per molecule of the lipid in the lamellae of this invention is actually measured ("$MMAM_{actual}$"), it is found to be at least 20% less than the corresponding $MMAM_{expected}$ value. That is, the mean area occupied by each of the lipid molecules in a glycerolipid/complementarily shaped lipid lamellae of this invention is at least about 20% less than would have been expected based upon the mean molecular areas of the individual lipids, as determined in accordance with the above equation. Accordingly, a "complementarily shaped lipid" is also a lipid which, when combined in a lamella with a glycerolipid in the proportions set forth herein, results in an $MMAM_{actual}$ of the lipids in the lamella that is at least about 20% less than the corresponding $MMAM_{expected}$ value.

Specific complementarily shaped lipids include, without limitation: neutral sterols; anionic sterol derivatives such as phosphate, sulfate, and organic dicarboxylic acid salt derivatives; cardiolipin; diarachidonoyl phosphatidylethanolamine ("DAPE"); and, combinations of these lipids. Additional complementarily shaped lipids can readily be identified by ordinarily skilled artisans given the teachings of this invention, for example, by identifying lipids which are cone-shaped, have packing parameters of greater than about 1, and which afford to the glycerolipid/complementarily shaped lipid combination an $MMAM_{actual}$ value, determined as described herein, that is at least about 20% less than the corresponding $MMAM_{expected}$ value, calculated as described herein.

Preferred complementarily shaped lipids are neutral sterols, anionic sterol derivatives and combinations of neutral sterols and anionic sterol derivatives, preferably at an about 5:1 molar ratio of neutral sterol to anionic sterol derivative. More preferably, the complementarily shaped lipid is the neutral sterol cholesterol, the anionic sterol derivative cholesterol sulfate or a combination of cholesterol and cholesterol sulfate. Complementarily shaped lipids are preferably combined with glycerolipids in this invention's lamellae at a ratio of about 30–50 mole percent glycerolipid to about 50–70 mole percent complementarily shaped lipid. More preferably, the ratio is about 40 mole percent glycerolipid to about 60 mole percent complementarily shaped lipid. Accordingly, in the most preferred embodiments of this invention, the lipid lamella consists essentially of about 40 mole percent of the glycerolipid ET-18OCH$_3$ and about 60 mole percent of a complementarily shaped lipid that is cholesterol, cholesterol sulfate or a 5:1 molar ratio combination of cholesterol with cholesterol sulfate.

Figure 3:
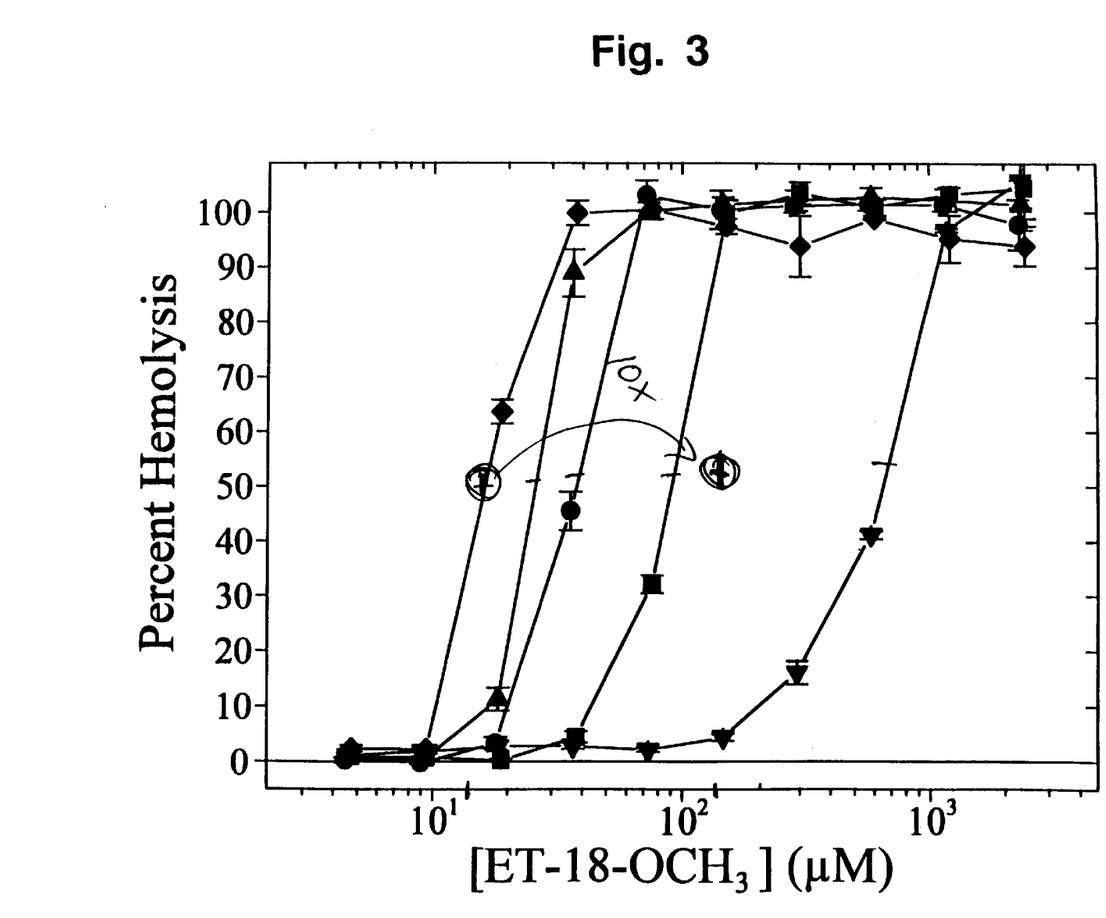

MMAM values have been calculated and determined (see below, and FIGS. 3A and 3B) for two-component lipid systems containing the glycerolipid ET-18-OCH$_3$ and the lipids palmitoyloleoyl phosphatidylcholine ("POPC"), dioleoyl phosphatidylcholine ("DOPC"), dioleoyl phosphatidylethanolamine ("DOPE") and cholesterol ("CHOL"), at various mole percentages of the two lipids. ET-18-OCH$_3$ combinations with POPC and DOPC exhibit, at most, a 10–15% MMAM reduction, i.e., a 10–15% difference between the MMAM$_{expected}$ value and the corresponding MMAM$_{actual}$, across the range of lipid concentrations examined. ET-18-OCH$_3$/DOPE combinations exhibit an MMAM reduction of less than about 20%.

However, for combinations of ET-18-OCH$_3$ and cholesterol at ET-18-OCH$_3$ concentrations of between about 30 and 50 mole percent, MMAM$_{actual}$ values are greater than 20% less than the corresponding MMAM$_{expected}$ values. For example, a 40 mole % ET-18-OCH$_3$/60 mole % CHOL combination exhibits an MMAM reduction of about 35%, while a 50 mole %/50 mole % combination exhibits a 42% MMAM reduction. Accordingly, substitution of cholesterol for DOPE in the lipid combinations, at the same lipid concentration, makes a significant difference to the degree of MMAM reduction obtained. Such differences in MMAM reductions between ET-18-OCH$_3$/CHOL and ET-18-OCH$_3$/DOPE combinations cannot be predicted based on art knowledge of CHOL and DOPE, because both of these lipids are cone-shaped, and both have packing parameters of about 1.2–1.3. Nevertheless, CHOL combines with ether lipids so as to achieve MMAM reductions of greater than about 20%, while DOPE does not. Hence, CHOL is a "complementarily shaped lipid," while DOPE is not.

The hemolytic activity of ET-18-OCH$_3$/CHOL, DOPE, POPC or DOPC liposomes, prepared as described below in Example 2, have also been examined, as described hereinbelow in Example 3. Results, presented hereinbelow in FIG. 3, are in the form of the ET-18-OCH$_3$ concentration in the various liposomes required to achieve hemolysis of 50% of the red blood cells present in a sample (H$_{50}$). The data indicate that hemolysis was least for the ET-18-OCH$_3$/cholesterol formulations with the H$_{50}$ value for these liposomes being 661 μM (micromolar). This formulation was over 7 times less hemolytic than the ET-18-OCH$_3$/DOPE liposomes, which exhibited an H$_{50}$ of 91 μM; the ET-18-OCH$_3$/DOPE and ET-18-OCH$_3$/POPC liposomes had similar H$_{50}$ values (38 and 26 μM, respectively).

Preferably, the lamella of this invention is a bilayer, more preferably, a liposomal bilayer. "Liposomes" are self-assembling structures having either a single lipid bilayer (unilamellar liposomes, "ULVs"), or multiple lipid bilayers (multilamellar liposomes, "MLVs"). Preferably, the liposome of this invention is either a multilamellar liposome, or a unilamellar liposome having an average size of about 25–200 nm. Liposomes can be made by a variety of methods (for a review, see, for example, Deamer and Uster (1983)). These methods include without limitation: Bangham's method for making multilamellar liposomes (MLVs); Lenk's, Fountain's and Cullis' methods for making MLVs with substantially equal interlamellar solute distribution ("SPLVs;" see, for example, U.S. Pat. Nos. 4,522,803, 4,588,578, 5,030,453, 5,169,637 and 4,975,282); and Papahadjopoulos et al.'s reverse-phase evaporation method (U.S. Pat. No. 4,235,871) for preparing oligolamellar liposomes ("REVs"). ULVs can be produced from MLVs by such methods as sonication (see Papahadjopoulos et al. (1968)) or extrusion (U.S. Pat. Nos. 5,008,050 and U.S. Pat. No. 5,059,421). The liposome of this invention can be produced by the methods of any of these documents, the contents of which are incorporated herein by reference.

Various methodologies, such as sonication, homogenization, French Press application and milling can be used to prepare liposomes of a smaller size from larger liposomes. Extrusion (see U.S. Pat. No. 5,008,050) can be used to size reduce liposomes, that is to produce liposomes having a predetermined mean size by forcing the liposomes, under pressure, through filter pores of a defined, selected size. Tangential flow filtration (see W089/008846), can also be used to regularize the size of liposomes, that is, to product liposomes having a population of liposomes having less size heterogeneity, and a more homogeneous, defined size distribution. Liposome sizes can be determined by a number of readily practiced techniques, such as quasi-electric light scattering, and with equipment, e.g., Nicomp® particle sizers. The contents of the above-cited documents are incorporated herein by reference.

Moreover, liposomes of this invention can be dehydrated, stored and then reconstituted such that a substantial portion of its contents are retained. Liposomal dehydration generally requires use of a hydrophilic drying protectant such as a disaccharide sugar, e.g., sucrose or maltose, at both the inside and outside surfaces of the liposome bilayers (see U.S. Pat. No. 4,880,635, the contents of which are incorporated herein by reference). This hydrophilic compound is generally believed to prevent the rearrangement of the lipids in the liposome, so that the size and contents are maintained during the drying procedure and through subsequent rehydration. Appropriate qualities for such drying protectants are that they be strong hydrogen bond acceptors, and possess stereochemical features that preserve the intramolecular spacing of the liposome bilayer components. Alternatively, the drying protectant can be omitted if the liposome preparation is not frozen prior to dehydration, and sufficient water remains in the preparation subsequent to dehydration.

Liposomes of this invention can contain one or more additional bioactive agents, that is, one or more bioactive agents in addition to the bioactive glycerolipid. "Bioactive agents" are any compounds or compositions of matter which can be administered to animals. These include agents having biological activity in the animals, as well as those useful for imaging or other forms of diagnosis. Bioactive agents include, but are not limited to: antiviral, antibacterial, antifungal, antiparasitic, antimetabolic, antiglaucomic, anti-inflammatory or antineoplastic compounds, carbohydrates, amino acids, peptides, proteins, immunoglobulins, immunomodulators, dyes, toxins, enzymes, hormones, neurotransmitters, glycoproteins, radiolabels, radiopaque compounds, fluorescent compounds, cell receptor proteins, cell receptor ligands, mydriatic compounds, vasodilators, bronchodilators, local anesthetics, growth promoting agents, regenerative agents and the like.

Liposomes can be loaded with one or more biologically active agents by solubilizing the agent in the lipid or aqueous phase used to prepare the liposomes. Alternatively, ionizable bioactive agents can be loaded into liposomes by first forming the liposomes, establishing an electrochemical potential, e.g., by way of a pH gradient, across the outermost liposomal bilayer, and then adding the ionizable agent to the aqueous medium external to the liposome (see Bally et al. U.S. Pat. No. 5,077,056 and W086/01102, the contents of which are incorporated herein by reference). Preferably, the additional bioactive agent is an anti-inflammatory or anti-cancer agent.

Compositions of this invention comprise, in addition to the glycerolipid/complementarily shaped lipid, a pharmaceutically acceptable carrier. Such carriers are generally acceptable for use in connection with the administration of therapeutic or diagnostic agents to animals. Pharmaceutically acceptable carriers are formulated according to a number of factors well within the purview of the ordinarily skilled artisan to determine and account for, including without limitation: the particular agent being administered, as well as its concentration, stability and intended bioavailability; the disease, disorder or condition being treated or diagnosed with the composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, Nairn (1985)). Typical pharmaceutically acceptable carriers used in parenteral bioactive agent administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and anti-oxidants.

Compositions of this invention can be administered to mammals by any of the standard means generally accepted in the art for doing so. Routes of administration, e.g., intravenous, intra-arterial, subcutaneous, intramuscular or intraperitoneal administration, are chosen with regard to a number of factors well within the purview of ordinarily skilled artisans, given the teachings of this invention, to determine and account for. Such factors include, without limitation: the age, body mass and general health of the subject being treated; the intended bioavailability of the drug; the particular form of disease being treated; the carrier used; and, the dose of therapeutic agent administered.

As described hereinabove, bioactive glycerolipids of this invention can be therapeutically effective anticancer agents. Provision of the glycerolipids in combination with complementarily shaped lipids, in lamellar form, allows the glycerolipids' detergent-like activity to be directed against cancer cells while shielding normal cells, e.g., red blood cells, from adverse effect. Accordingly, a lipid lamella-containing composition of this invention can be used in the treatment of mammals, e.g., humans, afflicted with cancers, by administering to the afflicted mammals an amount of a composition which comprises an anticancer effective amount of the glycerolipid.

An "anti-cancer effective amount" of a glycerolipid is any amount of the lipid effective to inhibit, ameliorate, lessen or prevent establishment, growth, metastasis or invasion of one or more cancers in animals to which the ether lipids have been administered. Anticancer effective amounts are generally chosen in accordance with a number of factors, e.g., the age, size and general condition of the subject, the cancer being treated and the intended route of administration, and determined by a variety of means, for example, dose ranging trials, well known to, and readily practiced by, ordinarily skilled artisans given the teachings of this invention. Typically, the anticancer effective amount of the glycerolipid is from about 1 mg per kg of the subject's body weight to about 1000 mg/kg.

Cancers treatable with the composition of this invention include, without limitation leukemias, lymphomas, sarcomas and carcinomas, as well as brain, breast, stomach, prostate, colon and ovarian cancers. Mammals treated for cancers with compositions of this invention can also be administered additional bioactive agents, that is, one or more biologically active agents in addition to the ether lipid.

Bioactive glycerolipids of this invention can also be effective anti-inflammatory agents. Inflammation is a process of cytological and histological reactions occurring in affected blood vessels, and surrounding tissues, in response to an injury or abnormal physical, chemical or biological stimulation (see, e.g., *Stedman's Medical Dictionary (Illustrated)*, pp. 707–708). Inflammatory responses include local reactions and resulting morphological changes, destruction or removal of injurious materials and activation of repair mechanisms. Inflammation can be part of the process by which animals heal themselves, but it can also occur in response to abnormal physiological stimuli and can cause problems in the body. Joints, for example, become inflamed in arthritic conditions such as gout, rheumatoid arthritis and Lyme disease (see, e.g., *Stedman's Medical Dictionary (Illustrated)*, pp. 123–124).

Humoral inflammatory responses can be characterized by the extravasation of cells to the location of the agent inducing the response, that is, exit of cells from the circulatory system to the site of attack. Accordingly, the anti-inflammatory potentials of various biologically active agents can be assessed based upon their ability to inhibit extravasation. Extravasation, aid inhibition of extravasation, can be examined by a number of means, including the rat air pouch exudate model (see Tate et al. (1991), the contents of which are incorporated herein by reference). Following the model, rats having air pouches formed in their backs by subcutaneous air injection are administered an inflammation-inducing agent, e.g., fMLP, such that an inflammatory condition is established; cells then enter the air pouch from the surrounding vasculature. Determining the presence of the cells with, and without administration of a particular bioactive agent is an indication of the agent's anti-inflammatory activity.

Inflammatory responses, and the anti-inflammatory action of potential anti-inflammatory agents, can also be studied by a number of models directed to arthritis induction/inhibition, for example, the rat adjuvant arthritis model in which rats are administered an arthritis inducer, for example, 10 micrograms of Freund's adjuvant per kg of body weight. Inhibition of joint swelling so induced is thus another measure of the anti-inflammatory efficacy of a potential anti-inflammatory agent.

Accordingly, the lipid lamella-containing composition of this invention can also be used to treat animals afflicted with an inflammatory disorder, e.g., systemic inflammatory response syndrome, asthma or an arthritic disorder. Compositions of this invention are administered for the treat of inflammation such that an anti-inflammation effective amount of the glycerolipid is given to the treatment subject.

An "anti-inflammation effective amount" of a glycerolipid is any amount of the lipid effective to ameliorate, lessen, inhibit or prevent an inflammatory response in an animal administered the lipid. Typically, the anti-inflammatory effective amount of the glycerolipid is from about 1 mg of the ether lipid per kg of the animal's body weight to about 1000 mg/kg.

Animals treated for cancer, inflammation or other diseases, disorders or conditions according to the practice of this invention can be administered one or more additional bioactive agents, that is, one or more biologically active agents in addition to the glycerolipid. Such additional bioactive agents can be administered either separately from the glycerolipid/complementarily shaped lipid, or as part of the same composition that contains the lipid lamella composed of these lipids.

This invention will be better understood from the following Examples. However, those of ordinary skill in the art will readily understand that these examples are merely illustrative of the invention as defined in the claims which follow thereafter.

EXAMPLES

Example 1

Mean Molecular Area per Molecule ("MMAM") Measurement

The mean molecular area per molecule of formulations containing the ether lipid ET-18-OCH$_3$ was determined using a Langmuir-Blodgett mini-trough equipped with a dual barrier mechanism and a Wilhelmy balance, all obtained from KSV Instruments (Trumbull, Conn.). ET-18-OCH$_3$ formulations were prepared from lipid powders that were dissolved in a solvent system of hexane:ethanol 9:1. Single lipid solutions and mixtures were made to contain an overall lipid concentration of approximately 1.5 mM which was quantitated precisely by phosphate (Chen et al., 1956) and cholesterol assays (Rudel & Morris, 1973). Monolayers were formed by dropwise addition of sample on to the aqueous surface (10 mM HEPES, 150 mM NaCl buffer, pH 7.2) at the center of the trough. Sample was added until the surface pressure just started to rise above zero, at which time the exact volume of sample added was recorded. After waiting three minutes for solvent evaporation and monolayer stabilization, the surface area of the monolayer was reduced at a rate of 15 cm$^2$/min, and surface pressure was recorded. The solution level was maintained 1 mm below the top edge of the trough to avoid leakage; contact was maintained with the barriers (composed of Delrin) due to their hydrophilic nature.

Figure 1:
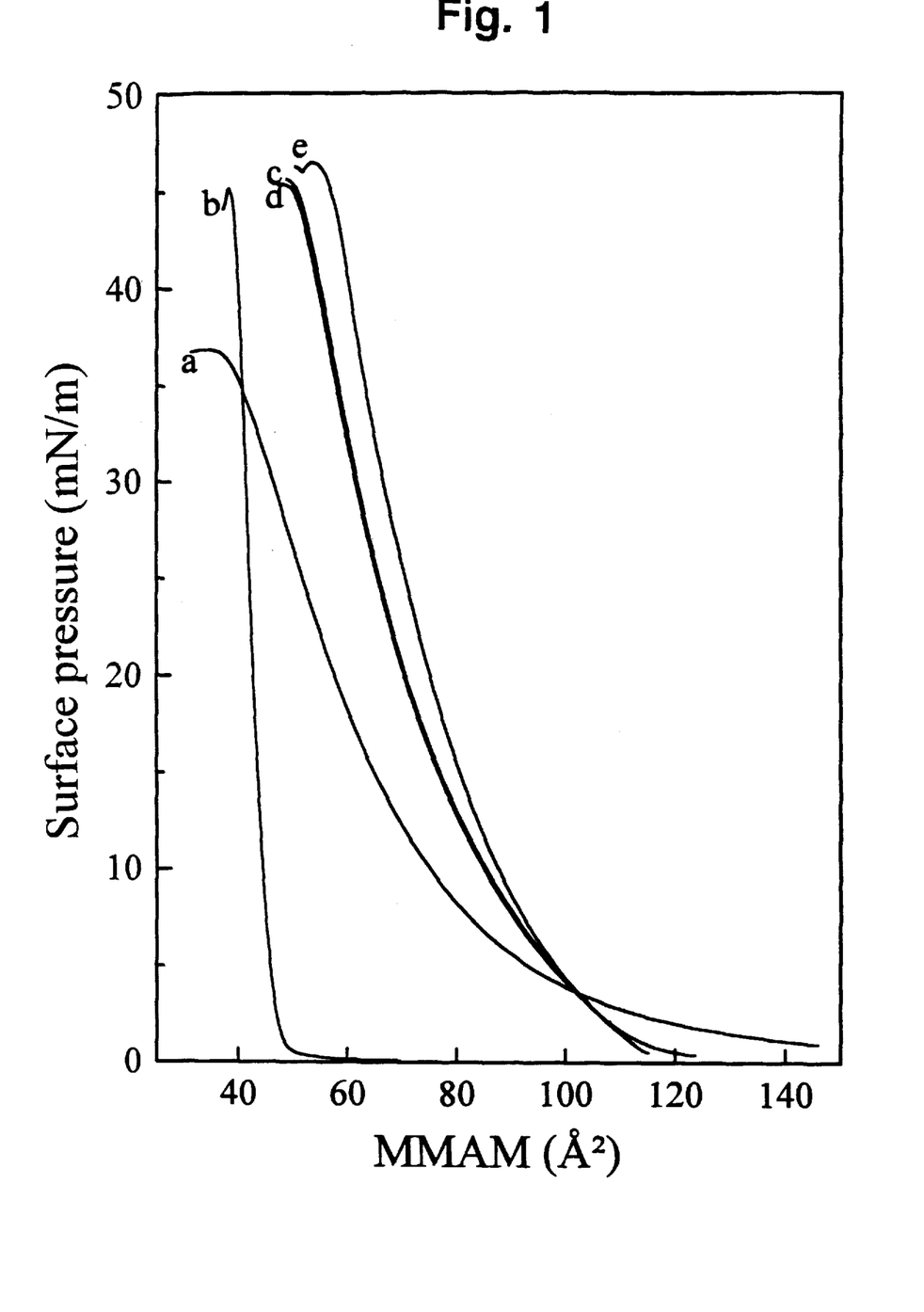

Pressure vs. area curves were compiled from data obtained as described above (see FIGS. 1 and 2), and MMAM values were determined by extrapolating the steepest portion of the curve to the value at zero surface pressure. The highest collapse pressure measured for any lipid in this study ($\leq 47$ mN/m) was well below the values attained with disaturated PC molecules (>62 mN/m) indicating that the collapse pressure was not an artifactual consequence of a technical limitation. All experiments were done at 23° C. Area versus surface pressure profiles were obtained for combinations of EL-18 and the lipids cholesterol, POPC, DOPC or DOPE. Cholesterol and DOPE both have an inverted cone shape; it has previously been shown, with NMR and X-ray studies, that CHOL and DOPE form lamellar phase structures when mixed with the cone-shaped lipid lyso-PC (see Rand et al., 1975; Madden & Cullis, 1982; Wu et al., 1991). As the surface area was reduced, surface pressure increased as the lipids packed into an organized oriented monolayer, each characteristic for that lipid; at high surface pressure, the monolayers collapsed. MMAMs (A$_0$) were determined for each lipid by extrapolation of the steepest portion of the curves to the value at zero surface pressure; and are as follows: ET-18-OCH$_3$: 72.8 Å$^2$; CHOL: 44.8 Å$^2$; DOPE: 82.3 Å$^2$; POPC: 82.0 Å$^2$; and, DOPC: 82.0 Å$^2$.

Figure 2:
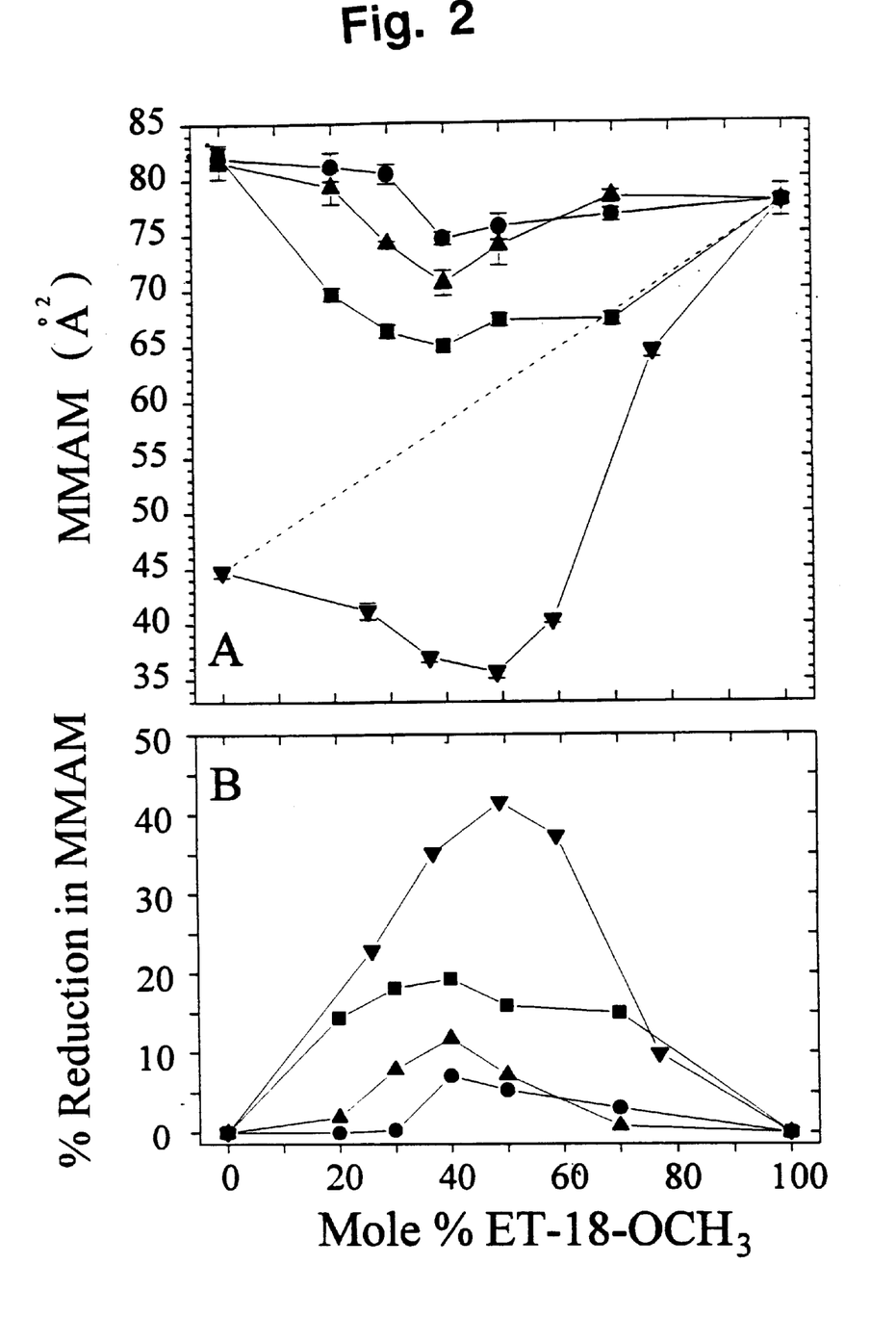

MMAM values of combinations of ET-18-OCH$_3$ with CHOL, DOPE, POPC and DOPC, at various mole percentages of each lipid, were obtained from the surface area-vs.-pressure curves shown in FIG. 2. The order for the percent reductions in MMAM values for the various ET-18-OCH$_3$/lipid combinations was cholesterol>>DOPE>POPC>DOPC. MMAM reductions afforded the lipid combination by DOPE were, at most, less than 20%. However (see FIG. 3A), a 1:1 ET-18-OCH$_3$/CHOL combination had an actual MMAM ~25 Å$^2$ less than the expected value (represented in the figure by the dashed line). The much larger reduction afforded the lipid combination by cholesterol, as compared to DOPE, was surprising given that both cholesterol and DOPE have an inverted cone-shape.

Example 2

Liposome Preparation

All phospholipids were purchased from Avanti Polar Lipids (Alabaster, Ala.). Cholesterol was purchased from Sigma Chemical Co. (St. Louis, Mo.); all lipids and reagents used were of the highest purity available. Liposomes were prepared by first mixing the appropriate lipids in solvent, drying the lipid to a thin film using vacuum rotary evaporation, and hydrating the resulting film with buffer solution (10 mM HEPES, 150 mM NaCl, pH 7.4). The resulting dispersions were used without further processing for NMR studies. For hemolysis studies, the lipid dispersions were then repeatedly extruded through polycarbonate Nucleopore® membranes (Nuclepore Corp., Pleasanton, Calif.) of defined pore size. Liposomes were first passed 10 times through a membrane of 0.2 μm pore size and then 10 passes through a membrane of 0.1 μm pore size. For ET-18-OCH$_3$/cholesterol, the mixtures were first passed through a 0.4 μm pore size filter 10 times before proceeding to the 0.2 μm pore size filter and finally the 0.1 μm pore size filter. Liposome size was determined by quasi-elastic light scattering using a Nicomp® Model 270/370 Submicron Particle Sizer from Pacific Scientific (Menlo Park, Calif.).

First, the phosphorus NMR signal of hydrated handshaken dispersions for the ET-18-OCH$_3$/lipid systems was examined to confirm the existence of lamellar phase (see FIG. 2). The phosphorus NMR spectra for ET-18-OCH$_3$ at 40 mole % with both cholesterol and DOPE at 23° C. and 37° C., were typical of lamellar phase lipid (Gruner, 1992). For DOPC and POPC mixtures with ET-18-OCH$_3$, there was an additional isotropic component on top of the broader lamellar signature. The spectrum resembled that for mixtures of small and large liposomes (Hope et al., 1986) and the line width appeared to be too broad (3.6–3.9 ppm at half height) to be ET-18-OCH$_3$ micelles (Kumar et al., 1988). In order to determine whether this component was due to mixed micellar structures or small vesicular structures, the fraction that would not form a plug on top of the solution (the mixtures floated) upon centrifugation was collected, and the ratio of ET-18-OCH$_3$ to lipid was examined by TLC (as described below in Example 5). The ratios were essentially the same as that for the bulk sample indicating that the structures were small liposomes, and not ET-18-OCH$_3$-rich micellar structures.

Example 3
Hemolysis

Liposomes containing 40 mole % ET-18-OCH$_3$ were prepared as described in Example 2. All liposomes were extruded, in order to assure uniform size distribution. Extrusion was more difficult (higher pressure required) for the ET-18-OCH$_3$/cholesterol mixture, which had a final size distribution (77 nm) that was slightly larger than that for the other samples (40 nm); however, the ratio of lipids in the final preparation was not different from that found prior to extrusion.

Hemolysis was assessed as previously described (Perkins et al., 1992). Briefly, each sample was serially diluted with buffer solution and 0.3 ml of each diluted solution was mixed with 0.3 ml of washed human red blood cells [4% in PBS (v/v)]. For controls, 0.3 ml of the red blood cell suspension was mixed with either 0.3 ml of buffer solution (negative hemolysis control) or 0.3 ml of distilled water (positive hemolysis control). Samples and standards were placed in a 37° C. incubator and agitated for 20 hours. Tubes were centrifuged at low speed (2000 g) for 10 minutes to pellet RBCs. Two hundred $\mu$l of the supernatant was removed and mixed with 1 ml of water. Hemolysis was quantitated by absorbance at 550 nm using a Shimadzu 2101 UV-Vis Scanning Spectrophotometer (Shimadzu Corp., Kyoto, Japan). One hundred percent hemolysis was defined as the maximum amount of hemolysis obtained from free ET-18-OCH$_3$.

FIG. 3 displays the hemolysis profiles for the four ET-18-OCH$_3$ liposome preparations, as well as for free ET-18-OCH$_3$. Hemolysis was least for the ET-18-OCH$_3$/cholesterol liposomes, with the concentration of ET-18-OCH$_3$ that yielded 50% hemolysis (H$_{50}$) being 661 $\mu$M. This formulation was over 7 times less hemolytic than the ET-18-OCH$_3$/DOPE liposomes, in which the H$_{50}$ of ET-18-OCH$_3$ was 91 $\mu$M. The ET-18-OCH$_3$/DOPC and ET-18-OCH$_3$/POPC formulations exhibited similar H$_{50}$ values (38 and 26 $\mu$M, respectively); the H$_{50}$ value for free ET-18-OCH$_3$ was (16 $\mu$M). Hemolytic activity of ET-18-OCH$_3$ small unilamellar liposomes ("SUVs") formulated at 40 or 60 mole % with cholesterol was compared. The 60 mole % ET-18-OCH$_3$ SUVs were as hemolytic as free EL-18-OCH$_3$. This confirmed our suspicion that ET-18-OCH$_3$, like lyso PC (Kumar, 1991; Kumar et al., 1988), does not form stable liposome structures above a 1:1 stoichiometry.

Example 4
Phosphorus Nuclear Magnetic Resonance (NMR) Spectroscopy

Spectra were obtained at 121.51 MHz on a Bruker AC300 NMR Spectrometer (Bruker Instruments, Billerica, Mass.) at either 23° C. or 37° C. 16 K points were acquired with a sweep width of 50 kHz using a 6 microsecond pulse. The average of 3000 acquisitions was processed with 50 Hz line broadening. Liposome samples were made by hydrating dried films of mixed lipids (see above). For NMR, ET-18-OCH$_3$ purchased from Alexis Corp. (San Diego, Calif.) was used. Samples contained a total of 20 mg/ml of ET-18-OCH$_3$ (approximately 60 mg/ml total lipid) except for the ET-18-OCH$_3$/cholesterol mixtures which contained 40 mg/ml ET-18-OCH$_3$ (60–90 mg/ml total lipid). The results of phosphorous NMR studies of ET-18-OCH$_3$ at a 40 mole percent concentration with both cholesterol and DOPE, at 23 deg. C; and at 37 deg. C., demonstrated that the lipids were in the lamellar phase. For DOPC and POPC mixtures with ET-18-OCH$_3$, there was an additional isotropic component on top of the broader lamellar signature.

Example 5
Thin Layer Chromatography (TLC)

Aqueous samples were first mixed with methanol and chloroform in the ratio 0.8:2:1 to form a single monophase. An aliquot of this was then applied to a silica gel plate which was run in chloroform/methanol/water (65:25:4) and then developed with iodine vapor. Standards of each lipid were also run.

What is claimed is:

1. A pharmaceutical composition comprising:

(a) a pharmaceutically acceptable carrier; and, (b) a lamella comprising a lipid which consists essentially of:

(i) a glycerolipid having the formula:

(ii) a complementarily shaped lipid, wherein:

$R^1$ is a group having the formula $Y_1Y_2$;

$Y_1$ is $(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}$;

the sum of n1+2n2+n3+2n4+n5+2n6+n7+2n8+n9 is an integer of from 9 to 23;

n1 is zero or an integer of from 1 to 23, n3 is zero or an integer of from 1 to 20, n5 is zero or an integer of from 1 to 17, n7 is zero or an integer of from zero to 14 and n9 is zero or an integer of from 1 to 11;

each of n2, n4, n6 and n8 is independently zero or 1;

$Y_2$ is $CH_3$ or $CO_2H$;

Z is oxygen or sulfur;

the glycerolipid comprises from about 30 mole percent to about 50 mole percent of the lipid;

the complementarily shaped lipid comprises from about 50 mole percent to about 70 mole percent of the lipid; and, the MMAM$_{actual}$ of the lipid is at least about 20% less than the MMAM$_{expected}$ of the lipid.

2. The composition of claim 1, wherein $R^1$ is $(CH_2)_{n1}CH_3$.

3. The composition of claim 2, wherein $R^1$ is $(CH_2)_{17}CH_3$.

4. The composition of claim 1, wherein Z is O.

5. The composition of claim 1, wherein the glycerolipid is:

6. The composition of claim 1, wherein the complementarily shaped lipid is a neutral sterol, anionic sterol derivative selected from the group consisting of sulfate, phosphate and organic dicarboxylic acid salt derivatives, cardiolipin or diarachidonoyl phosphatidylethanolamine.

7. The composition of claim 6, wherein the complementarily shaped lipid is the neutral sterol cholesterol.

8. The composition of claim 6, wherein the complementarily shaped lipid is the anionic sterol derivative cholesterol sulfate.

9. The composition of claim 6, wherein the complementarily shaped lipid comprises a neutral sterol and an anionic sterol derivative.

10. The composition of claim 9, wherein the neutral sterol is cholesterol and the anionic sterol derivative is cholesterol sulfate.

11. The composition of claim 9, wherein the neutral sterol and anionic sterol derivative are present in the lipid at a respective molar ratio of about 5:1.

12. The composition of claim 1, wherein the glycerolipid comprises about 40 mole percent of the lamellar lipid and the complementarily shaped lipid comprises about 60 mole percent of the lamellar lipid.

13. The composition of claim 1, wherein the glycerolipid is and wherein the complementarily shaped lipid is cholesterol.

14. The composition of claim 13, wherein the glycerolipid comprises about 40 mole percent of the lipid and the complementarily shaped lipid comprises about 60 mole percent of the lipid.

15. The composition of claim 1, wherein the glycerolipid is and wherein the complementarily shaped lipid is cholesterol sulfate.

16. The composition of claim 15, wherein the glycerolipid comprises about 40 mole percent of the lipid and the complementarily shaped lipid comprises about 60 mole percent of the lipid.

17. The composition of claim 1, wherein the glycerolipid is wherein the complementarily shaped lipid comprises cholesterol and cholesterol sulfate and wherein cholesterol and cholesterol sulfate are present in the lipid of a respective molar ratio of about 5:1.

18. The composition of claim 17, wherein the glycerolipid comprises about 40 mole percent of the lipid and the complementarily shaped lipid comprises about 60 mole percent of the lipid.

19. The composition of claim 1, wherein the lamella is a liposomal bilayer.

20. The composition of claim 19, wherein the liposome is a unilamellar liposome having an average size of about 50–250 nm.

21. The composition of claim 19, wherein the liposome is a multilamellar liposome.

* * * * *